(12) United States Patent
Devaraj et al.

(10) Patent No.: US 12,017,993 B2
(45) Date of Patent: Jun. 25, 2024

(54) PREPARATION OF HALOGEN ANALOGS OF PICLORAM

(71) Applicant: CORTEVA AGRISCIENCE LLC, Indianapolis, IN (US)

(72) Inventors: Jayachandran Devaraj, Zionsville, IN (US); Nugzar Ghavtadze, Montreal (CA); Nicholas M. Irvine, Westfield, IN (US); Jeremy Kister, Carmel, IN (US); Melissa Lee, Indianapolis, IN (US); Ronald B. Leng, Midland, MI (US); Rongrong [Mandy] Lin, Edmonton (CA); Rong Ling, Edmonton (CA); Noormohamed M. Niyaz, Indianapolis, IN (US); Abraham D. Schuitman, Zionsville, IN (US); Aaron A. Shinkle, Brownsburg, IN (US); Siyu Tu, Midland, MI (US); Gregory T. Whiteker, Carmel, IN (US); Chunming Zhang, Zionsville, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 24 days.

(21) Appl. No.: 17/808,368

(22) Filed: Jun. 23, 2022

(65) Prior Publication Data
US 2022/0371997 A1    Nov. 24, 2022

Related U.S. Application Data

(62) Division of application No. 17/276,169, filed as application No. PCT/US2019/051650 on Sep. 18, 2019, now Pat. No. 11,401,242.

(60) Provisional application No. 62/733,285, filed on Sep. 19, 2018.

(51) Int. Cl.
*C07D 213/803*    (2006.01)

(52) U.S. Cl.
CPC ................. *C07D 213/803* (2013.01)

(58) Field of Classification Search
CPC ................................. C07D 213/803
USPC ...................................... 546/310
See application file for complete search history.

(56) References Cited

U.S. PATENT DOCUMENTS

| | | | |
|---|---|---|---|
| 11,401,242 B2 | 8/2022 | Devaraj et al. | |
| 2014/0274701 A1 | 9/2014 | Eckelbarger et al. | |
| 2016/0340332 A1 | 11/2016 | Berl | |
| 2023/0167061 A1 | 6/2023 | Hazari et al. | |

FOREIGN PATENT DOCUMENTS

| | | |
|---|---|---|
| DE | 102016122812 | 5/2018 |
| WO | 2007034325 A1 | 3/2007 |
| WO | 2011068895 A1 | 6/2011 |
| WO | 2011146287 | 11/2011 |
| WO | 2012103045 | 2/2012 |
| WO | WO2014/151009 A1 * | 3/2012 |
| WO | 2012103047 | 8/2012 |
| WO | 2014018502 | 1/2014 |
| WO | 2017201377 A1 | 11/2017 |

OTHER PUBLICATIONS

Sakthivel, K. et al., "Direct SNAr amination of fluorinated imidazo[4,5-c]-pyridine nucleosides: efficient syntheses of 3-fluoro-3-deazaadenosine analogs", Tetrahedron Letters, 2005, 3883-3887, vol. 46, Elsevier.
Joshi, Sukesha; Sharma, Sunita; Gaba, Jyoti; Kaur, Pardeep; "A facile synthesis and antimicrobial activity of different phthalimides containing heterocyclic moiety", Indian Journal of Heterocyclic Chemistry, 2018, vol. 28—No. 4, pp. 459-465, Published by Connect Journals, India.
Abdel-Hafez, Atef Abdel-Monem, "Synthesis and anticonvulsant evaluation of N-substituted isoindolinedione derivatives", Archives of Pharmacal Research, 2004, vol. 27—Issue 5, pp. 495-501, Published by Springer Science +Business Media, Korea.
Brocklehurst C.E., et al., "Microtiter Plate (MTP) Reaction Screening and Optimization of Surfactant Chemistry: Examples of Suzuki-Miyaura and Buchwald-Hartwig Cross-Couplings in Water," Organic Process Research & amp; Development, US, Oct. 2, 2018, vol. 22, No. 10, pp. 1453-1457, DOI: 10.1021/acs.oprd.8b00200, ISSN 1083-6160, XP055737457.
Griffin W C., et al., "Calculation Of HLB Values Of Non-Ionic Surfactants," Journal Of the Society Cosmetic Chemists, Society of Cosmetic Chemists, US, May 14, 1954, vol. 5, No. 249, pp. 249-256, ISSN 0037-9832, XP000671451.
International Preliminary Report on Patentability for International Application No. PCT/US2019/051650, dated Oct. 14, 2020, 28 Pages.
International Preliminary Report on Patentability for International Application No. PCT/US2021/031226, dated Nov. 24, 2022, 8 Pages.
International Search Report and Written Opinion for International Application No. PCT/US2019/051650, dated Nov. 13, 2019, 8 Pages.
International Search Report and Written Opinion for International Application No. PCT/US2021/031226, dated Jul. 20, 2021, 11 Pages.
International Search Report and Written Opinion for International Application No. PCT/US2022/076700, dated Nov. 29, 2022, 9 pages.

(Continued)

*Primary Examiner* — Taofiq A Solola

(57) ABSTRACT

Methods for preparing 5-fluoro-6-(bromo or chloro)picloram analogs, or derivatives thereof, from picloram acid, picloram ester, or the nitrile analog of picloram are provided. The methods include chemical process steps that: (1) introduce a phthaloyl group onto the 4-amino substituent of picloram acid, picloram ester, or the nitrile analog of picloram, (2) add 2 fluorine atoms at the 5,6-positions of the pyridine ring using halex fluorination chemistry, (3) remove the phthaloyl group, hydrolyze the ester or nitrile substituent, and add chlorine or bromine to the 6-position by treatment with an acid and water, and finally, (4) esterify the 5-fluoro-6-(bromo or chloro)picloram acid produced in step (3) to a 5-fluoro-6-(bromo or chloro)picloram ester.

3 Claims, No Drawings

(56) References Cited

OTHER PUBLICATIONS

Klumphu P., et al., "Nok". A Phytosterol-Based Amphiphile Enabling Transition-Metal-Catalyzed Couplings in Water at Room Temperature, The Journal of Organic Chemistry, Feb. 7, 2014, vol. 79, No. 3, pp. 888-900, 43 Pages, Jan. 21, 2014, DOI: 10.1021/jo401744b, ISSN 0022-3263, XP055465377.

Lipshutz B.H., et al., "Catalysis in the Service of Green Chemistry: Nobel Prize-Winning Palladium-Catalysed Cross-Couplings, Run in Water at Room Temperature," Platinum Metals Review, Apr. 1, 2012, vol. 56, No. 2, pp. 62-74, 24 Pages, DOI: 10.1595/147106712X629761, ISSN 0032-1400, XP055099205.

Lipshutz B.H., et al., "Designer"-Surfactant-Enabled Cross-Couplings in Water at Room Temperature, Aldrichimica Acta., Jan. 1, 2012, vol. 45, No. 1, pp. 3-16, XP055099441.

Lipshutz B.H., et al., "TPGS-750-M: A Second-Generation Amphiphile for Metal-Catalyzed Cross-Couplings in Water at Room Temperature," The Journal of Organic Chemistry, Jun. 3, 2011, vol. 76, No. 11, pp. 4379-4391, 35 Pages, DOI: 10.1021/jo101974u, ISSN 0022-3263, XP055290855.

\* cited by examiner

PREPARATION OF HALOGEN ANALOGS OF PICLORAM

PRIORITY

This application is a division of U.S. Ser. No. 17/276,169 filed Mar. 15, 2021, which claims priority to PCT/US2019/051650 filed Sep. 18, 2019, which claims priority to U.S. 62/733,285 filed Sep. 19, 2018, which are hereby incorporated herein by reference in their entirety.

BACKGROUND

Picloram (I; X, Y=Cl), a member of the picolinic acid family of herbicides, is an auxin herbicide that offers very good control of broadleaf weeds in rangeland, grass pastures, forestry and industrial settings (12$^{th}$ Edition of the Pesticide Manual, 2000). Picloram has also served as a raw material for the production of another useful auxin herbicide known as aminopyralid (I, X=Cl, Y=H).

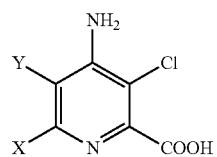

I

SUMMARY

Described herein are methods for preparing 5,6-dihalo analogs of picloram from picloram or derivatives (esters or the nitrile) thereof. Specifically, 5-fluoro-6-(bromo or chloro)picloram analogs, or derivatives (esters or the nitrile) thereof, of Formula II may be prepared.

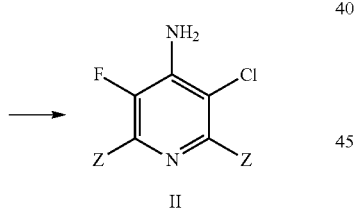

II wherein X=Cl or Br, Z is COOR or CN, and R is $C_1$-$C_{12}$ alkyl, $C_6$-$C_{12}$ arylalkyl, $C_3$-$C_{12}$ alkynyl, $C_1$-$C_3$ alkyl substituted with CN, or H.

Compounds of Formula II are useful intermediates employed in the synthesis of herbicides as described in WO 2012/103044 A1 and WO 2012/103041 A2.

The methods involve first combining a compound of Formula III with a phthaloyl halide of Formula IIIa or a phthalic anhydride of Formula IIIb, and, optionally a base,

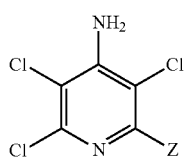

III

-continued

IIIa

IIIb wherein each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4; and W is Cl or Br. Then isolating a compound of Formula IV from the first step

IV and combining the isolated compound of Formula IV with a fluorinating compound or a fluorinating mixture of compounds. Next a compound of Formula V

V is isolated and combined with HCl or HBr and water. Finally, a compound of Formula II is isolated.

Another aspect of the present disclosure are the novel compounds produced by the described methods, viz., the compounds:

wherein X=Cl or Br, Z is COOR, and R is $C_2$-$C_{12}$ alkyl, $C_6$-$C_{12}$ arylalkyl, $C_3$-$C_{12}$ alkynyl, $C_1$-$C_3$ alkyl substituted with CN, or H; and

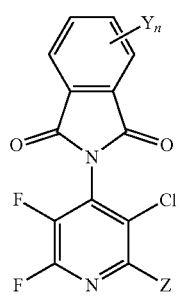

wherein Z is COOR or CN, and R is H, $C_1$-$C_{12}$ alkyl, or $C_6$-$C_{12}$ arylalkyl; and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4.

DETAILED DESCRIPTION

A method for preparing 5-fluoro-6-(bromo or chloro) picloram analogs, or derivatives thereof, of Formula II from a Picloram ester or nitrile of Formula III is provided. As illustrated in Scheme 1, the method includes chemical process steps that: (1) introduce a cyclic imide group, such as phthaloyl, to the 4-amino substituent by reaction of the compound of Formula III with a diacid halide, such as phthaloyl chloride, or an acid anhydride, such as phthalic anhydride, (2) place 2 fluorine atoms at the 5,6-positions of the pyridine ring by use of fluorination chemistry, and (3) remove the cyclic imide group, hydrolyze the ester or nitrile substituent, and introduce a halogen atom at the 6-position by treatment with an acid HX and water, wherein X is Cl or Br.

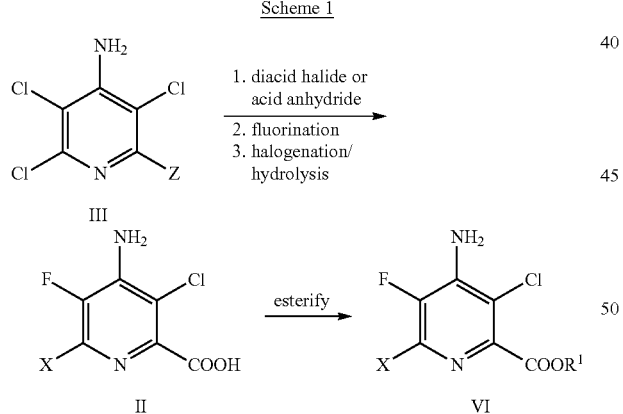

Scheme 1 wherein X is Cl or Br, Z is COOR or CN, R is $C_1$-$C_{12}$ alkyl, and $R^1$ is $C_2$-$C_{12}$ alkyl, $C_6$-$C_{12}$ arylalkyl, $C_3$-$C_{12}$ alkynyl, or $C_1$-$C_3$ alkyl substituted with CN.

I. Definitions

The compound of Formula IV, wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, 4, 5, 6, 7, or 8 may be represented by the following chemical structures. The phthaloyl structures may be represented by either of the two versions of the phthaloyl structure which are considered to be identical in all respects.

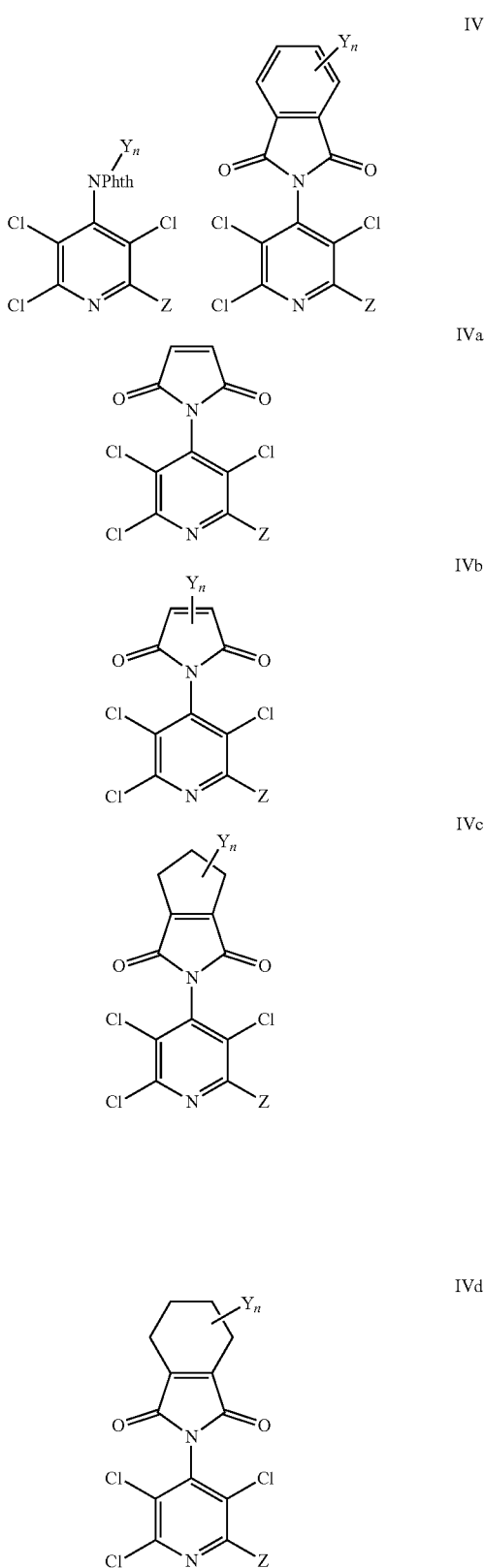

-continued

IVe
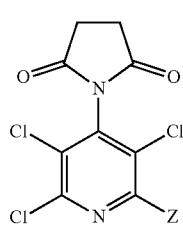

IVf
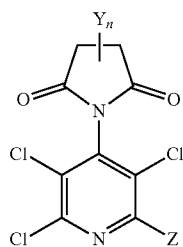

IVg
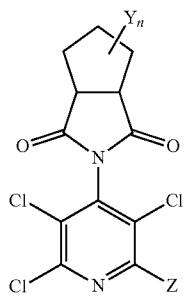

IVh
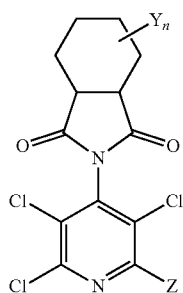

An aspect of the invention is a compound of formula IV wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4.

An aspect of the invention is a compound of formula IVa wherein Z is $CO_2R$ or CN, R is a $C_1$-$C_{12}$ alkyl or $C_6$-$C_{12}$ arylalkyl.

An aspect of the invention is a compound of formula IVb wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, or 2.

An aspect of the invention is a compound of formula IVc wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, 4, 5, or 6.

An aspect of the invention is a compound of formula IVd wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, 4, 5, 6, 7, or 8.

An aspect of the invention is a compound of formula IVe wherein Z is $CO_2R$ or CN, R is a $C_1$-$C_{12}$ alkyl or $C_6$-$C_{12}$ arylalkyl.

An aspect of the invention is a compound of formula IVf wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4 and wherein 2 Y groups may be bonded to one another to form a ring.

An aspect of the invention is a compound of formula IVg wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, 4, 5, or 6.

An aspect of the invention is a compound of formula IVh wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, 4, 5, 6, 7, or 8.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. In some embodiments, the heteroaryl group can be a pyridyl, pyrimidyl or a triazinyl group. The aryl or heteroaryl groups may be unsubstituted or substituted with one or more chemical moieties. Examples of suitable substituents include, for example, amino, halo, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkyl sulfonyl, $C_1$-$C_{10}$ alkoxycarbonyl, $C_1$-$C_6$ carbamoyl, hydroxycarbonyl, $C_1$-$C_6$alkylcarbonyl, aminocarbonyl, $C_1$-$C_6$alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_4$ alkyl, $C_1$-$C_4$ alkoxy, $C_1$-$C_4$ haloalkyl, $C_1$-$C_4$ haloalkoxy, and nitro.

As used herein, the term "alkyl," refers to linear alkyl, branched alkyl, or cyclic alkyl groups. Cyclic alkyl groups may also include those groups referred to as cycloalkyl or alicyclic groups such as, for example, cyclohexyl or cyclopentyl.

As used herein, the term "$C_6$-$C_{12}$ arylalkyl," also includes the benzyl group (i.e., $CH_2Ph$).

II. Preparation of Phthalimide IV

The first step of the method to prepare the compound of Formula II is shown in Scheme 3 and involves the conversion of the compound of Formula III, wherein Z is $CO_2R$ or CN, and R is a $C_1$-$C_{12}$ alkyl or $C_6$-$C_{12}$ arylalkyl, to the corresponding cyclic imide of Formula IV by reaction of III with a diacid halide, such as phthaloyl halide of Formula Ma or an acid anhydride, such as phthalic anhydride of Formula IIIb, wherein X is Cl or Br, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4.

Scheme 2

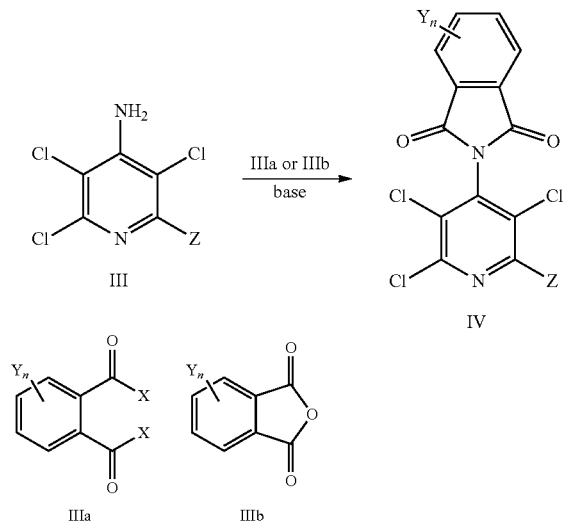

The process step to make IV can be conducted in solvents such as, but not limited to, polar aprotic solvents like acetonitrile (ACN), toluene, dimethylformamide (DMF), propionitrile, or benzonitrile, ethers such as THF, 2-methyl-THF, dioxane, cyclopentyl methyl ether (CPME), monoethyleneglycol ethers, diethyleneglycol ethers, monopropyleneglycol ethers or dipropyleneglycol ethers, or ketones such as methyl isobutyl ketone (MIBK), and mixtures thereof. The temperature range for conducting this process step may range from about 25° C. to about 100° C., from about 25° C. to about 90° C., from about 25° C. to about 80° C., from about 25° C. to about 70° C., from about 25° C. to about 60° C., or from about 25° C. to about 55° C., and the reaction may be conducted over a time period ranging from about 1 hour to about 72 hours, from about 1 hour to about 48 hours, from about 1 hour to about 24 hours, from about 1 hour to about 12 hours, from about 1 hour to about 6 hours, from about 2 hours to about 24 hours, from about 4 hours to about 24 hours, from about 2 hours to about 12 hours, or from about 4 hour to about 12 hours.

From about 1 to about 3, about 1 to about 2.5, about 1 to about 2, about 1 to about 1.5, about 1 to about 1.4, about 1 to about 1.3, about 1 to about 1.2, or from about 1 to about 1.1 molar equivalents of the phthaloyl halide or the phthalic anyhdride can be used in the process. A base can be used to capture the HX acid liberated in the process when using a phthaloyl halide and may be selected from bases like trialkylamines such as, but not limited to, trimethylamine, triethylamine, or tripropylamine, and nitrogen containing heterocycles such as pyridine, and alkyl substituted pyridines such as 2-picoline or 3-picoline. Phthalimide IV can be isolated from the process by employing standard isolation and purification techniques. A base can be optionally used with the phthalic anhydride in the process to make IV.

In one embodiment, the use of an acylation catalyst such as, but not limited to, DMAP (4-(dimethylamino)-pyridine) or N-methylimidazole, may be used in the preparation of IV from Ma or Mb.

In another embodiment of the first step of the method to prepare the compound of Formula II as shown in Scheme 3, the first step may be preceded by a step whereby a carboxylic acid of Formula III, wherein Z is $CO_2H$, is contacted with an alcohol ROH, wherein R is a $C_1$-$C_{12}$ alkyl or $C_6$-$C_{12}$ arylalkyl, in the presence of an acid or acid-forming compound to provide the ester of Formula III, wherein Z is $CO_2R$. The ester produced in this manner can then be used to prepare the phthalimide of Formula IV as described herein.

III. Preparation of Difluorophthalimide V

The second step of the method to prepare the compound of Formula II involves the conversion of the compound of Formula IV, wherein Z=$CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4, to the corresponding difluorophthalimide of Formula V by treatment of IV with a fluorinating compound or a fluorinating mixture of compounds in the presence of a solvent as shown in Scheme 4.

Scheme 3

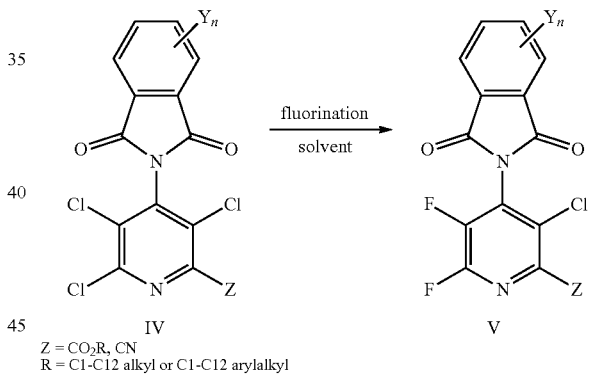

Z = $CO_2R$, CN
R = C1-C12 alkyl or C1-C12 arylalkyl

The fluorinating compound or fluorinating mixture of compounds for use in the second step of the method may be selected from the group including KF (potassium fluoride), CsF (cesium fluoride), and TMAF (tetramethylammonium fluoride), and mixtures thereof, or a mixture of tetramethylammonium chloride (TMAC) with KF or CsF.

The amount of the fluorinating compound or the fluorinating mixture of compounds used relative to the substrate of Formula IV to prepare the compound of Formula V may range from about 2 to about 8 molar equivalents of KF, from about 2 to about 8 molar equivalents of CsF, or from about 2 to about 6 molar equivalents of TMAF. In one embodiment the fluorinating mixture of compounds includes from about 2 to about 10 molar equivalents of KF or CsF and from about 0.01 to about 2.0 molar equivalents of TMAC.

Solvents that may be suitable for use with the fluorinating compounds or the fluorinating mixture of compounds to prepare V include, but are not limited to, polar aprotic solvents such as acetonitrile (ACN), propionitrile (PCN), benzonitrile (BCN), dimethylsulfoxide (DMSO), N,N-dimethylformamide (DMF), sulfolane, dimethylacetamide (DMAC), 1,1-dimethyl-2-imidizolidinone (DMI), N,N'-dimethylpropyleneurea (DMP), N-methylpyrrolidinone (NMP), tetrahydrofuran (THF), 2-methyl-THF, dioxane, monoethyleneglycol ethers, diethyleneglycol ethers, monopropyleneglycol ethers, or dipropyleneglycol ethers, and mixtures thereof.

In one embodiment, the fluorination of IV may be conducted with KF or CsF in DMF solvent. In another embodiment, the fluorination of IV may be conducted with KF or CsF in DMSO solvent. In another embodiment, the fluorination of IV may be conducted with KF or CsF, and TMAC in DMF solvent. In another embodiment, the fluorination of IV may be conducted with KF or CsF, and TMAC in DMSO solvent. In another embodiment, the fluorination of IV may be conducted with TMAF in THF solvent.

It is generally preferred to conduct the fluorination of IV to prepare V under anhydrous or near-anhydrous conditions. These anhydrous or near-anhydrous conditions may be obtained by prior drying of the reactants and solvents. One way to dry the reactants and/or solvents is by removal by distillation of a portion of the solvent prior to conducting the fluorination reaction.

The fluorination reaction to produce the compound of Formula V may be conducted at a temperature of at least about 0° C., at least about 10° C., at least about 20° C., at least about 25° C., at least about 30° C., at least about 40° C., at least about 50° C., at least about 60° C., at least about 70° C., at least about 80° C., at least about 90° C., or at least about 100° C. The fluorination reaction to produce the compound of Formula V may be conducted at a temperature of about 0° C. to about 50° C., from about 10° C. to about 50° C., from about 25° C. to about 50° C., from about 15° C. to about 150° C., from about 25° C. to about 150° C., from about 35° C. to about 125° C., from about 45° C. to about 115° C., from about 55° C. to about 110° C., from about 65° C. to about 110° C., from about 75° C. to about 110° C., from about 85° C. to about 110° C., from about 90° C. to about 110° C., from about 50° C. to about 100° C., from about 60° C. to about 100° C., from about 70° C. to about 100° C., from about 25° C. to about 90° C., from about 25° C. to about 80° C., about 25° C. and about 110° C., from about 25° C. to about 70° C., or from about 25° C. to about 60° C.

Isolation of the compound of Formula V from the fluorination reaction mixture may be conducted by removing the insoluble salts by filtration and then adding water to the resulting filtrate to precipitate the desired product, which may be purified by employing standard purification techniques.

IV. Preparation of 4-Amino-3-chloro-6-(chloro or bromo)-5-fluoropicolinic acid II The next step of the method to prepare the compound of Formula II involves the conversion of the compound of Formula V, wherein Z is $CO_2R$ or CN, R is a $C_1$-$C_{12}$ alkyl or $C_6$-$C_{12}$ arylalkyl, and each Y substituent is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, or nitro, wherein n is 1, 2, 3, or 4, to the compound of Formula II wherein X is Cl or Br. This conversion is shown in Scheme 5 and involves treating compound V with a hydrohalide acid HX and water, wherein X is Cl or Br, to provide the compound of Formula II, wherein X is Cl or Br.

Scheme 4

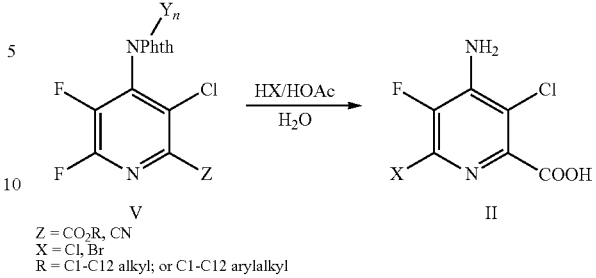

Z = $CO_2R$, CN
X = Cl, Br
R = C1-C12 alkyl; or C1-C12 arylalkyl

The conversion involves halide exchange of the 6-fluoro substituent by the HX acid to provide either a 6-chloro or 6-bromo substituent, hydrolysis of the Z substituent to a carboxylic acid, and removal of the phthaloyl group by hydrolysis to regenerate the 4-amino substituent. A co-solvent of acetic acid (HOAc) is useful to help facilitate this conversion. The HX salt of compound II (wherein X is Cl or Br) may also form in this reaction.

This step may be conducted in two stages, wherein the first stage is conducted at lower temperature and/or with no or limited amounts of water to achieve halide exchange of the 6-fluoro substituent, and the second stage is conducted at higher temperature and/or with more water to achieve hydrolysis of the phthaloyl group and the ester (or cyano) substituent).

In some examples, the amount of water included in this step relative to the starting compound of Formula V on a molar basis may range from about 1 to about 30, from about 1 to about 20, from about 1 to about 10, from about 1 to about 8, from about 1 to about 6, from about 1 to about 4, from about 2 to about 5, from about 2 to about 4, or from about 3 to about 4 molar equivalents of water per mole of compound V.

In other examples, the amount of acid HCl or HBr included in this step relative to the starting compound of Formula V on a molar basis may range from about 50 to about 1, from about 40 to about 1, from about 30 to about 1, from about 20 to about 1, from about 10 to about 1, from about 8 to about 1, from about 6 to about 1, from about 3 to about 1, from about 2 to about 1, or from about 3 to about 2 molar equivalents of HCl or HBr per mole of compound V.

In further examples, the reaction to produce the compound of Formula II from the compound of Formula V may be conducted at a temperature from about 50° C. to about 150° C., from about 60° C. to about 140° C., from about 70° C. to about 130° C., from about 80° C. to about 120° C., from about 90° C. to about 120° C., or from about 100° C. to about 120° C.

A by-product of the reaction to produce the product of Formula II from the compound of Formula V is phthalic acid or a substituted phthalic acid, which is derived from hydrolytic cleavage of the phthaloyl group of compound V. Methods of separating or removing the phthalic acid or the substituted phthalic acid from the reaction mixture containing the compound of Formula II may include, but are not limited to, solvent extraction with an organic, an aqueous, or an organic-aqueous solvent, or differential aqueous solubility at certain pH levels or ranges.

In another example of this process step, the HBr or HCl salt of compound II (wherein X is Cl or Br) may be formed in small amounts and be present in the isolated product of Formula II. This compound (IIa) may be reduced or removed from product II by solvent extractions of crude product II with water or with alcohol-water mixtures such as methanol-water.

V. Preparation of esters of 4-Amino-3-chloro-6-(chloro or bromo)-5-fluoropicolinic acid The acid of Formula II, wherein X is Cl or Br, may be converted into the ester of Formula VI, wherein X is Cl or Br, and $R^1$ is $C_1$-$C_{12}$ alkyl, $C_6$-$C_{12}$ arylalkyl, $C_3$-$C_{12}$ alkynyl or $C_1$-$C_3$ alkyl substituted with CN. Methods to prepare ester VI from acid II include, but are not limited to,

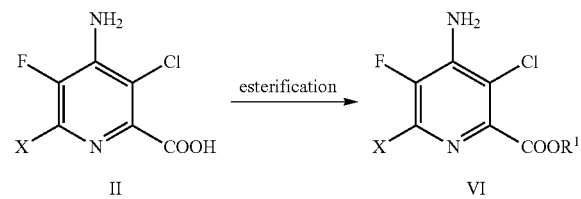

acid catalyzed esterification of acid II with an alcohol, and alkylation of acid II with an alkyl or benzyl halide under basic conditions.

VI. Isolation/Purification

After preparation of the compound of Formula II by the process described herein, the product may be isolated by employing standard isolation and purification techniques. For example, the crude product may be isolated using standard methods as described herein and purified by crystallization or recrystallization using a single solvent or a mixture of two or more solvents. Also, the crude product may be purified by washing it with or stirring it in a one, two or three-component solvent mixture. In one embodiment, the crude product may be purified by stirring it in an aqueous alcohol solvent mixture which can also be described as an aqueous alcohol slurry treatment.

The crude product of Formula II may also be purified by dissolving it in one solvent to form a solution and then adding a second solvent to the solution to cause the product of Formula II to crystallize out of the mixture of the two solvents.

The following examples are presented to illustrate the methods and compositions described herein.

EXAMPLES

Example 1a. Preparation of methyl 4-amino-3,5,6-trichloropicolinate

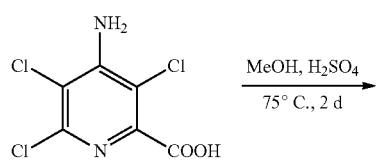

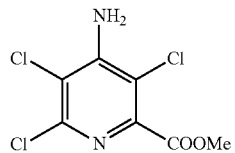

Picloram (100 g, 95% purity, 414 mmol, 1.0 eq.) was suspended in methanol (800 mL). Sulfuric acid (26 mL, 487 mmol, 1.2 eq.) was added at room temperature slowly. The reaction mixture was stirred at 75° C. (oil bath with condenser) for 2 days. The mixture was cooled down to room temperature. Water (200 mL) was added. The light brown solution was concentrated to remove methanol. The resulting residue was dissolved in water (200 mL) and EtOAc (600 mL), cooled with ice-bath and neutralized with 4N NaOH and sat. $NaHCO_3$ solution to pH=8. EtOAc layer was separated and aqueous layer was washed with EtOAc. Combined organic layer was dried and concentrated to yield compound 2 (71 g, 67% yield) as pale yellow solid. HPLC purity: 99.9%. Mp. 125.8-126.1° C.; $^1$H NMR ($CDCl_3$) δ 5.38 (br s, 2H), 3.97 (s, 3H).

Example 1b. Preparation of iso-propyl 4-amino-3,5,6-trichloropicolinate

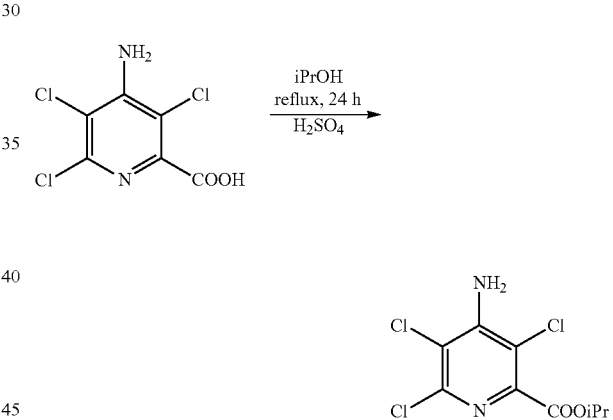

Picloram (4.66 g, 95%, 18.3 mmol, 1 eq.) was suspended in isopropyl alcohol (30 mL). Concentrated sulfuric acid (0.6 g, 6.1 mmol, 0.33 eq.) was added at room temperature. The reaction mixture was then heated at reflux for 18 hr. The reaction was then cooled to room temperature. 23% Aqueous $K_2CO_3$ (10 mL) was slowly added to the reaction mixture, and the mixture was stirred for 30 min. The reaction mixture was extracted with EtOAc (20 mL) and the organic phase was washed with 20 mL of saturated, aqueous brine. The organic phase was dried, the solvent was evaporated, and the residual solid was dried in the vacuum oven to give an off-white solid (4.9 g, 94%; HPLC purity: 96%). Mp 128.5-131.0° C.; $^1$H-NMR (400 MHz, $CDCl_3$): δ 5.35 (br s, 2H), 5.29 (septuplet, J=6.4 Hz, 1H), 1.39 (d, J=6.4 Hz, 6H) ppm.

Example 2a. Preparation of Phthalimide IV (Z=CO₂Me)

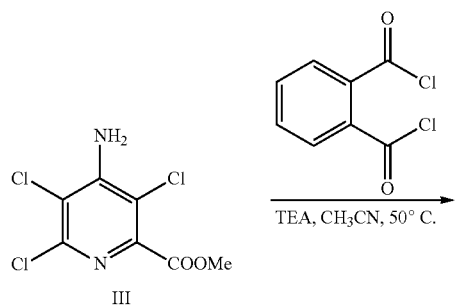

Compound III (Z=CO₂Me; 86 g, 337 mmol) was dissolved in acetonitrile (600 mL). Triethylamine (TEA, 94 mL, 673 mmol, 2.0 eq.) was then added at room temperature, followed by dropwise addition of phthaloyl chloride (65 mL, 404 mmol, 1.2 eq.). The reaction mixture was stirred at 50° C. overnight. Water (100 mL) was added to the mixture. The suspension was stirred for 1 h and filtered through filter paper. The solid was washed with water, and then hexane, and dried. The dry solid was suspended in toluene (200 mL) and the resulting mixture was concentrated to provide compound IV (85.1 g, 66% yield) as a pale yellow solid. HPLC purity: 97.7%. Mp. 185.3-185.9° C.; $^1$H NMR (CDCl₃) δ 8.02 (m, 2H), 7.88 (d, 2H, m), 4.02 (s, 3H).

Example 2b. Preparation of Phthalimide IV (Z=CN)

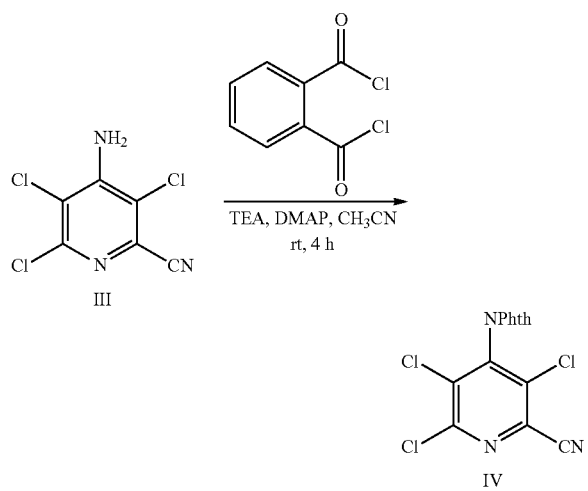

Compound III (Z=CN; 64.06 g, 288.0 mmol) was suspended in acetonitrile (960 mL). TEA (90.0 mL, 640.0 mmol, 2.2 eq.) and DMAP (3.52 g, 28.8 mmol, 0.1 eq.) were added at room temperature, followed by slow addition of phthaloyl chloride 2 (51.2 mL, 320 mmol, 1.1 eq.), maintaining internal temperature of the reaction less than 50° C. during the addition. The reaction mixture was stirred at room temperature for 4 h. Water (130 mL) was added to the reaction, the suspension was stirred for 30 min and filtered. The solid collected was washed with water (4×150 mL), hexane (2×100 mL) and dried to yield compound IV (Z=CN; 97.0 g, 96% yield) as a light purple solid, which was dissolved in dichloromethane (DCM) and passed through a silica gel pad to give an off-white solid with an HPLC purity: 99.6%. Mp. 233.7-234.8° C.; $^1$HNMR (400 mHz, DMSO-d₆): δ 8.14 (2H, m), 8.04 (2H, m).

Example 2c. Preparation of Phthalimide IV (Z=CO₂Me)

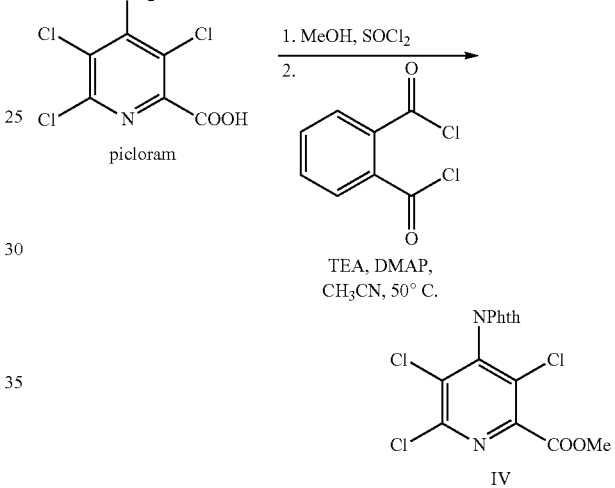

Picloram (105.25 g, 414.9 mmol, 95.2% purity, 1.0 eq.) was suspended in MeOH (650 mL) in a 3 L 3-neck flask equipped with mechanical stirrer and condenser. The mixture was vigorously stirred at room temperature. Thionyl chloride (0.90 mL, 12 mmol, 0.03 eq.) was added dropwise. The reaction mixture was stirred at 75° C. (external temperature) for 18 hours. The white suspension changed to light yellow clear solution after reaction. A sample was taken for HPLC analysis (96.7% methyl ester, 2.3% Picloram). After partially removing methanol to about 150 mL remaining, 500 mL toluene was added and co-evaporated at 40-55° C. under house vacuum to dryness. A sample was taken for $^1$H-NMR analysis and no MeOH or toluene remained. Then, 690 mL MeCN was added to form a turbid solution. To this solution TEA (134 mL, 959.0 mmol, 2.3 eq.) and DMAP (5.33 g, 43.6 mmol, 0.105 eq.) were added, followed by dropwise addition of phthaloyl chloride (77 mL, 479.5 mmol, 90% purity, 1.15 eq) to provide an orange reaction mixture (exothermic). At this step, the temperature was controlled below 55° C. by adjusting the addition rate. After addition was complete, the reaction mixture was stirred for another 2 hours. Water (200 mL) was then added to the mixture. The resulting suspension was stirred for 30 min and filtered. The wet cake collected on the funnel was washed with water (2×200 mL), hexanes (200 mL) and dried under vacuum to yield IV (154.4 g, 96% yield over 2 steps, HPLC purity: 98%) as a beige solid.

Example 2d. Preparation of Phthalimide IV (Z=CO₂iPr)

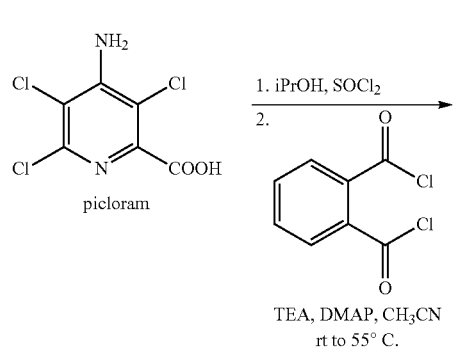

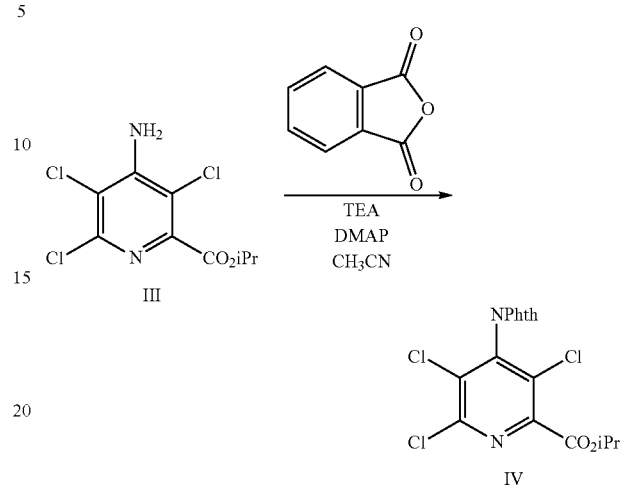

Step 1: A 3 L, 3-neck flask equipped with mechanical stirrer, condenser and addition funnel was charged with Picloram (100 g, 98.2% pure, 414.1 mmol, 1 eq.) and iPrOH (950 mL). SOCl₂ (15.1 mL, 207 mmol, 0.5 eq.) was added dropwise via addition funnel to the slurry at room temperature and then the reaction mixture was heated at reflux for 24 h. The reaction mixture was cooled down to room temperature, the solvent was evaporated to dryness and then co-evaporated with MeCN (2×100 mL) to yield a white solid (117.5 g crude). HPLC: 93.6% IV, 2.84% Picloram.

Step 2: A 3 L, 3-neck flask equipped with mechanical stirrer, thermometer and addition funnel was charged with the white solid isolated above, MeCN (700 mL), TEA (150 mL, 1076.7 mmol, 2.6 eq.) and DMAP (5.05 g, 41.4 mmol, 0.1 eq.). Phthaloyl chloride (90% pure, 73 mL, 455.51 mmol, 1.1 eq.) was added dropwise via addition funnel to maintain the temperature below 55° C. The reaction mixture was stirred at room temperature for 3 h. Water (250 mL) was added to the mixture. The resulting suspension was stirred for 30 min and filtered through filter paper. The solid was washed with water (3×100 mL) and hexane (2×100 mL) and dried. The solid was co-evaporated with toluene (2×250 mL), dried, washed with hexanes (2×200 mL) and dried again to yield compound IV (151.5 g, 88% yield) as a pale, yellow solid. HPLC: 98.8% purity. Mp. 157.0-157.9° C.; ¹H-NMR (400 MHz, CDCl₃): δ 8.00-8.04 (m, 2H), 7.86-7.90 (m, 2H), 5.33 (septuplet, J=6.4 Hz, 1H), 1.42 (d, J=6.4 Hz, 6H) ppm.

Example 2e. Preparation of Phthalimide IV (Z=CO₂iPr)

Compound III (8.1 g, 27.6 mmol, 1.0 eq.) was suspended in CH₃CN (33 mL) in a 100 mL RBF equipped with magnetic stirrer and condenser. TEA (9.6 mL, 69.0 mmol, 2.5 eq.) and Phthalic anhydride (4.9 g, 33.1 mmol, 1.2 eq.) were added at rt, followed by DMAP (0.34 g, 2.76 mmol, 0.1 eq.). The yellow suspension was stirred at 80° C. (oil bath temperature) for 2 hours. Yellow clear solution was observed after 5 min in 80° C. oil bath. Additional Phthalic anhydride (4.0 g, 27.0 mmol, 1 eq.) was added to the reaction mixture at 80° C. The reaction mixture was stirred at 80° C. for another 4.5 h (total reaction time was 6.5 h). The reaction was cooled to rt and water (33 mL) was added to the mixture. The suspension was stirred for 30 min and filtered through filter paper. The wet solid was washed with water and hexane and dried at 55° C. in vacuum oven to yield 3 (9.8 g, 86% yield) as yellow solid. HPLC purity: 99.2%.

Example 2f. Preparation of Phthalimide IV (Z=CO₂iPr)

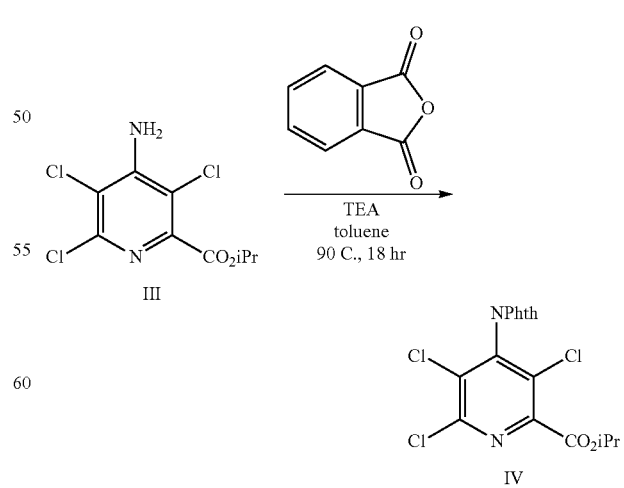

To a suspension of compound III (2.5 g, 8.82 mmol, 1.0 eq.) in toluene (11 mL) was added triethylamine (2.96 mL, 21.2 mmol, 2.5 eq.) and phthalic anhydride (3.26 g, 22.0 mmol, 2.5 eq.). The resulting suspension was stirred in a 90° C. oil bath for 18 h. The clear yellow solution was cooled gradually to room temperature to provide a thick beige slurry. Saturated NaHCO$_3$ solution (5 mL) was added slowly at room temperature and the resulting slurry was stirred in an ice water bath for 1 h. Solid was collected by vacuum filtration followed by water wash (2×5 mL). The wet solid was further dried in a vacuum oven at 55° C. for 5 h to provide product IV (3.1 g, 86% yield; HPLC purity: 99.5%) as off-white powdery solid.

Example 2g. Preparation of Phthalimide IV (Z=CO$_2$iPr)

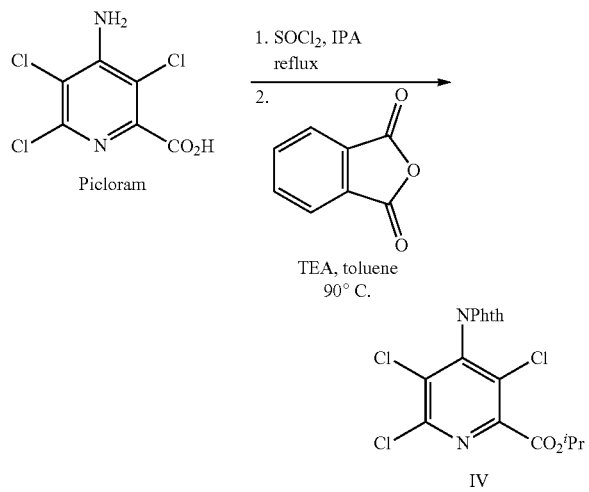

A 2 L flask was charged with Picloram (101.8 g, 98.2% purity, 0.414 mol, 1.0 eq.) and IPA (918.3 mL). SOCl$_2$ (15.6 mL, 97% purity, 0.21 mol, 0.5 eq.) was added and the reaction mixture was heated at reflux for 17 h. Then IPA (750 mL) was distilled off under atmospheric pressure. Toluene (600 mL) was added to the resulting solution. Distillation was continued and after another 2 h a mixture of IPA/toluene (600 mL) was distilled off at 81~110° C.

To the stirred suspension, TEA (144.3 mL, 1.04 mol, 2.5 eq.) was added followed by Phthalic anhydride (99% purity, 153.3 g, 1.04 mol, 2.5 eq.) in portions. The reaction mixture was heated at 88~93° C. for 17 h, cooled to room temperature. Sat. NaHCO$_3$ aq. (400 mL) was added slowly over 0.5 h while cooling to keep temperature below 20° C. After addition of sat. NaHCO$_3$ aq was finished the resultant slurry was stirred at room temperature for 2 h, filtered, washed with water (3×100 mL), and dried at 60° C. for 24 h to afford product IV (144.0 g, 84.2% yield; HPLC purity: 99.03%).

Example 3a. Preparation of Difluorophthalimide V (Z=CO$_2$Me)

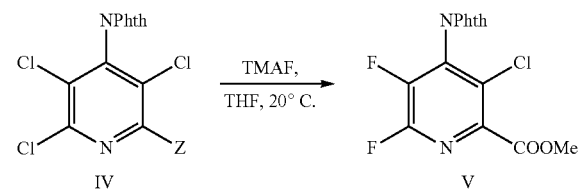

To compound IV (Z=CO$_2$Me; 5.00 g, 12.97 mmol) in a 250 mL, round-bottom flask under nitrogen was added anhydrous THF (100 mL) and tetramethylammonium fluoride (TMAF; 4.83 g, 51.87 mmol, 4 eq.; Aldrich) in one portion. The reaction mixture was stirred at room temperature for 5 h, cooled down to 0° C., quenched with water (400 mL) and stirred at 0° C. for 1 h. The solid product present was collected by filtration, washed with water (2×100 mL), and hexanes (3×100 mL), and dried to provide compound V (4.0 g, 87% yield) as a pale yellow solid. HPLC purity: 92.3% of V; Mp. 180.2-182.6° C.; $^1$H NMR (d$_6$-DMSO) δ 8.12 (d, 2H), 8.02 (d, 2H), 3.94 (s, 3H). F NMR (d$_6$-DMSO) δ −83.30, −133.05. Also contained 6.6% of the 3,5,6-trifluorinated side-product.

Example 3b. Preparation of Difluorophthalimide V (Z=CO$_2$Me)

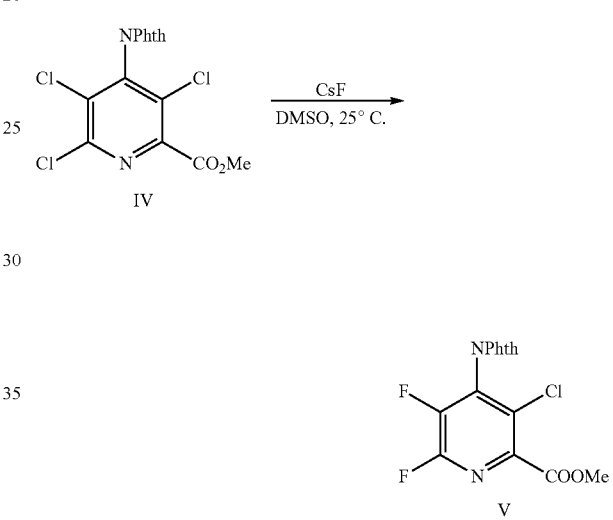

A mixture of CsF (82.7 g, 545 mmol) in DMSO (1.2 L) was distilled at 90° C. under in-house vacuum to remove 250 mL of DMSO. After cooling down to room temperature with N$_2$, compound IV (60.0 g, 156 mmol) was added in three portion. The mixture was vigorously stirred under N$_2$ for 27 h at 25° C., and then poured into ice water (3.6 L), stirred for 1 h, filtered, and the filtered solid washed with water (600 mL) and hexanes (300 mL), and dried to provide compound V (55 g, 100% crude) as an off-white solid. HPLC purity: 93.6% (contains 1.3% monofluoro side-product and 2.3% trifluoro side-product). The off-white solid was refluxed in MeOH (150 mL) for 30 min and filtered to give V (51.1 g, 92.7% yield) as a pale, beige solid: HPLC purity: 95.7%. Also contained 1.3% 6-monofluoro side-product and 1.7% 3,5,6-trifluoro side-product.

A sample of the pale, beige solid (Compound V, 1.0 g) was dissolved in a minimum amount of hot EtOAc (12.5 mL) and the resulting solution was diluted with 25 mL of methanol. The resulting solution was gradually cooled with stirring to room temperature and then was cooled in an ice/water bath. The mixture that formed was filtered, and the filtered solid was washed twice with 5 mL of MeOH and dried to yield Compound V (0.81 g, 81% recovery) as off-white, fine crystals. HPLC purity: 98.1%. Also contained 6-monofluoro side-product: 0.8% and 3,5,6-trifluoro side-product: 0.9%.

Example 3c. Preparation of Difluorophthalimide V (Z=CO$_2$iPr)

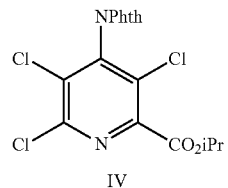

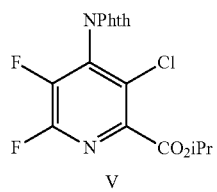

Solid potassium fluoride (12.7 g, 219 mmol; Sigma Aldrich) was added to a 1 L jacketed glass reactor which had been purged with nitrogen and was maintained with a nitrogen sweep on the headspace. The reactor was fitted with a 1" diameter, trayed distilling column. Then, 353.0 g of dimethylsulfoxide (DMSO; Fischer Scientific) was added to the reactor. The mixture was agitated at a rate of 350 RPM. A vacuum of approximately 40 mmHg was applied and the temperature of the reactor contents was increased to approximately 108° C. Approximately 100 mL of material was distilled with the distilling column and removed from the reactor. The temperature of the reactor contents were reduced to 75° C. and the water content was determined by Karl-Fischer analysis to be 51 ppm. The reactor was then charged with compound IV (24.9 g, 60.2 mmol) and the temperature was increased to 100° C. The reaction was held at 100° C. for approximately 7.5 hours. The reactor was then cooled to 75° C. and the reaction mixture was passed through a fritted filter to remove the solid salts. The filtered salts were washed with 44 g of DMSO and the filtrate and wash were added to a second vessel for crystallization. The second vessel was cooled to 12° C., the contents were agitated at 250 RPM, and 363 g of water was continuously added to the second vessel over approximately 2 hours. A mixture formed and was stirred for another one hour at 12° C., and the solid present was then collected by filtration, washed with about 68 g of water, and dried in a vacuum oven at 60° C. and 25 torr overnight. The resulting dry solid (21.5 g, 94% yield) provided 93.7% of the 5,6-di-F desired product (V) Mp: 115.8-117.1° C.; $^1$H NMR (400 MHz, CDCl$_3$): δ 8.00-8.06 (2H, m), 7.86-7.91 (2H, m), 5.32 (1H, septet, J=6.0 Hz), 1.42 (6H, d, J=6.0 Hz). $^{19}$F NMR (376 MHz, CDCl$_3$): −134.21 (d), −82.76 (d). Also contained 2.6% of the 3,5,6-trifluoro side-product and 2.0% of the 6-monofluoro side-product.

Example 3d. Preparation of Difluorophthalimide V (Z=CO$_2$iPr)

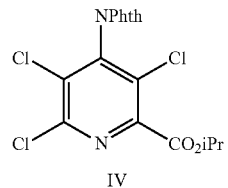

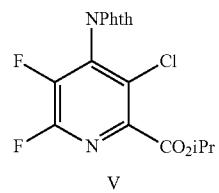

Solid potassium fluoride (7.68 g, 132 mmol; Sigma Aldrich) was added to a 1 L jacketed glass reactor which had been purged with nitrogen and was maintained with a nitrogen sweep on the headspace. The reactor was fitted with a 1" diameter, trayed distilling column containing 7 trays. Then, 211.7 g of dimethylformamide (DMF; Fischer Scientific) was added to the reactor followed by 41.6 g of toluene (Fischer Scientific). The solution was agitated at a rate of 275 RPM. A vacuum of approximately 350 mmHg was applied and the temperature of the reactor contents was increased to approximately 110° C. Approximately 75 mL of material was distilled with the distilling column and removed from the reactor by decreasing the pressure as material was distilled overhead. The temperature of the reactor contents was then reduced to 45° C. and the water content was determined by Karl-Fischer analysis to be 101 ppm. The reactor was then charged with compound IV (15.2 g, 36.7 mmol) and the temperature was increased to 100° C. The reaction was held at 100° C. for approximately 33 hours. The reactor was then cooled to 40° C. and the reaction mixture was passed through a fritted filter to remove the solid salts. The filtered salts were washed with 36.1 g of DMF and the filtrate and wash were added to a second vessel for crystallization. The second vessel was cooled to 10° C., the contents were agitated at 250 RPM, and 170 g of water were continuously added over approximately 2 hours. A mixture formed and was stirred for another 4 hours at 10° C., and the solid present was then collected by filtration, washed with about 44 g of water, and dried in a vacuum oven at 60° C. (25 torr) overnight. The resulting dry solid (12.0 g, 80% yield) provided 82.6% of the 5,6-di-F desired product (V). Also contained 1.1% of the 3,5,6-trifluoro side-product and 16.6% of the 6-monofluoro side-product.

Example 3e. Preparation of Difluorophthalimide V (Z=CO$_2$iPr)

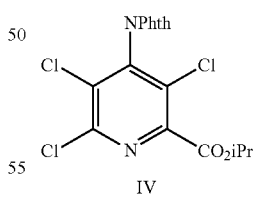

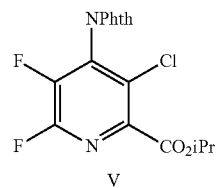

Solid potassium fluoride (11.15 g, 192 mmol; Sigma Aldrich) was added to a 1 L jacketed glass reactor which had been purged with nitrogen and was maintained with a nitrogen sweep on the headspace. The reactor was fitted with a 1" diameter, trayed distilling column containing 7 trays. Then, 207.2 g of dimethylsulfoxide (DMSO; Fischer Scientific) was added to the reactor followed by solid tetramethylammonium chloride (5.29 g, 48.3 mmol; TMAC, Sigma Aldrich). The mixture was agitated at a rate of 350 RPM. A vacuum of approximately 100 mmHg was applied and the temperature of the reactor contents was increased to approximately 100° C. Approximately 35 mL of material was distilled with the distilling column and removed from the reactor. The temperature of the reactor contents was then reduced to 45° C. and the water content was determined by Karl-Fischer analysis to be 102 ppm. The reactor was then charged with compound IV (19.8 g, 47.9 mmol) and the temperature of the reaction mixture was increased to 60° C. The reaction was held at 60° C. for approximately 3.5 hours and then was increased to 70° C. That temperature was held for approximately 8.5 hours at 70° C. and then was increased and held for one hour at 80° C. The reactor was then cooled to 75° C. and the reaction mixture was passed through a fritted filter to remove the solid salts. The filtered salts were washed with 50 g of DMSO and the filtrate and wash were added to a second vessel for crystallization. The second vessel was cooled to 21° C., the contents were agitated at 250 RPM, and 267 g of water were continuously added over approximately 2 hours. A mixture formed and was stirred for another one hour at 21° C., and the solid present was then collected by filtration, washed with about 66 g of water, and dried in a vacuum oven at 60° C. (25 torr) overnight. The resulting dry solid (15.5 g, 85% yield) provided 97.5% of the 5,6-di-F desired product (V). Also contained 1.7% of the 3,5,6-trifluoro side-product and 1.9% of the 6-monofluoro side-product.

Example 3f. Preparation of Difluorophthalimide V (Z=CO$_2$iPr)

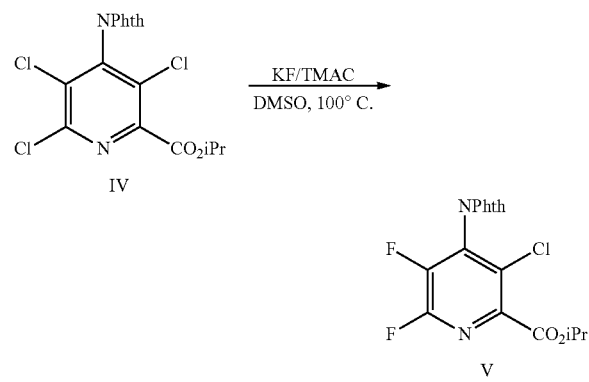

Solid potassium fluoride (12.7 g, 219 mmol; Sigma Aldrich) was added to a 1 L jacketed glass reactor which had been purged with nitrogen and was maintained with a nitrogen sweep on the headspace. The reactor was fitted with a 1" diameter, trayed distilling column containing 7 trays. Then, 408.9 g of dimethylsulfoxide (DMSO; Fischer Scientific) was added to the reactor followed by 34.6 g (110 mmol) of a solution of 35% tetramethylammonium chloride (TMAC) in methanol (SAChem). The mixture was agitated at a rate of 350 RPM. A vacuum of approximately 60 mmHg was applied and the temperature of the reactor contents was increased to approximately 100° C. Approximately 115 mL of material was distilled with the distilling column and removed from the reactor. The temperature of the reactor contents was reduced to 70° C. and 54 g more DMSO was added to the pot before restarting the distillation and collecting approximately 35 mL of additional distillate. The temperature of the reactor contents were reduced to 75° C. and the water content was determined by Karl-Fischer analysis to be 179 ppm. The reactor was then charged with compound IV (24.9 g, 60.2 mmol) and the temperature was increased to 100° C. The reaction was held at 100° C. for approximately 2.25 hours. The reactor was cooled to 75° C. and the reaction mixture was passed through a fritted filter to remove the solid salts. The filtered salts were washed with 116 g of DMSO and the filtrate and wash were added to a second vessel for crystallization. The second vessel was cooled to 14° C., the contents were agitated at 250 RPM, and 283 g of water were continuously added over approximately 2 hours. A mixture formed and was stirred for another 1 hour at 14° C., and the solid present was then collected by filtration, washed with about 64 g of water, and dried in a vacuum oven at 60° C. (25 torr) overnight. The resulting dry solid (22.5 g, 98% yield) provided 98.3% of the 5,6-di-F desired product (V). Also contained 3.8% of the 3,5,6-trifluoro side-product and 0.5% of the 6-monofluoro side-product.

Example 3g. Preparation of Difluorophthalimide V (Z=CO$_2$Et)

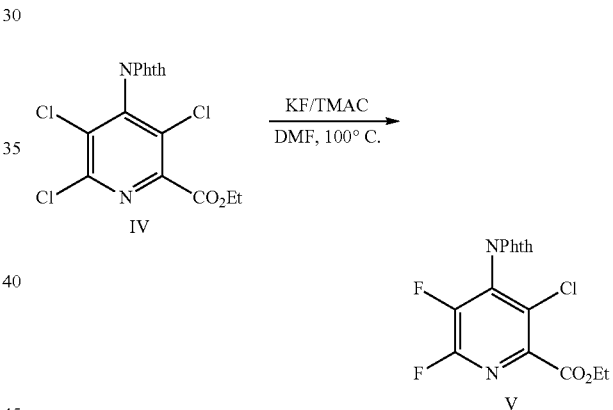

Solid potassium fluoride (5.9 g, 102 mmol; Sigma Aldrich) was added to a 1 L jacketed glass reactor which had been purged with nitrogen and was maintained with a nitrogen sweep on the headspace. The reactor was fitted with a 1" diameter, trayed distilling column containing 7 trays. Then, 139.5 g of dimethylformamide (DMF; Fischer Scientific) was added to the reactor followed by 15.8 g (50.4 mmol) of a solution of 35% tetramethylammonium chloride (TMAC) in methanol (SAChem). The solution was agitated at a rate of 350 RPM. A vacuum of approximately 90 mmHg was applied and the temperature of the reactor contents was increased to approximately 90° C. Approximately 75 mL of material was distilled with the distilling column and removed from the reactor. The temperature of the reactor contents was reduced to 45° C. and the water content was determined by Karl-Fischer analysis to be 105 ppm. The reactor was then charged with compound IV (10.05 g, 25.1 mmol) and the temperature was increased to 100° C. The reaction was held at 100° C. for approximately 4 hours. The reactor was cooled to 50° C. and the reaction mixture was passed through a fritted filter to remove the solid salts. The filtered salts were washed with 73 g of DMF and the filtrate and wash were added to a second vessel for crystallization. The second vessel was cooled to 2° C., the contents were agitated at 250 RPM, and 172.3 g of water was continuously added to the reaction mixture over approximately 2 hours in order to keep the temperature of the mixture below 10° C. A mixture formed and was stirred for another 1 hour at about 10° C., and the solid present was then collected by filtration, washed with about 35 g of water, and dried in a vacuum oven at 60° C. (25 torr) overnight. The resulting dry solid (6.44 g, 70% yield) provided 97.3% of the 5,6-di-F desired product (V). Mp: 111.2-116.7° C.; $^1$H NMR (400 MHz, CDCl$_3$): δ 8.00-8.04 (2H, m), 7.88-7.90 (2H, m), 4.47 (2H, q, J=6.8 Hz), 1.43 (3H, d, J=6.8 Hz); $^{19}$F NMR (376 MHz, CDCl$_3$): −133.57 (d), −82.54 (d). Also contained 2.4% of the 3,5,6-trifluoro side-product and 3.8% of the 6-monofluoro side-product.

Example 3h. Preparation of Difluorophthalimide V (Z=CO$_2$cHexyl)

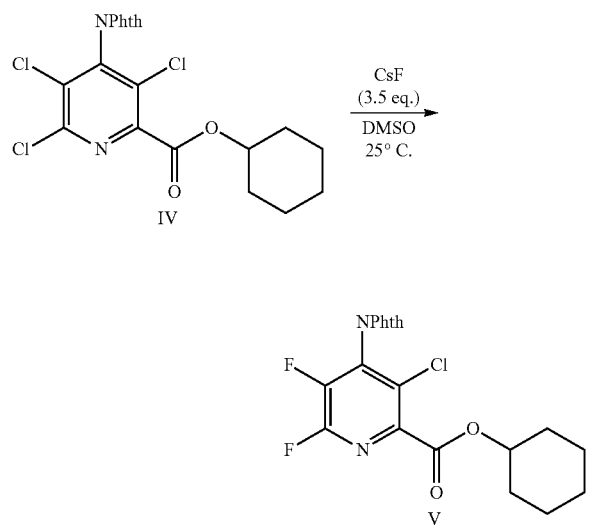

CsF (1.17 g, 7.70 mmol) was added to a 50 mL RBF equipped with stirring bar and distillation apparatus. Then 25 mL of dimethylsulfoxide (DMSO) was added. The flask was half-way merged to an oil bath. Vacuum (approximately 1 mm Hg) was connected to the distillation apparatus. Approximately 10 mL of DMSO was distilled out. Distillation apparatus was removed and the system was cooled with N2 balloon. When oil bath reached 25° C., compound 1 (1.0 g, 2.17 mmol) was added in one portion to the flask and flask was capped with rubber stopper and nitrogen balloon. The reaction mixture was stirred at room temperature for 24 h, poured into 50 mL ice-water, stirred for 30 min and product collected. The wet cake was washed with water (2×10 mL) and hexane (10 mL) and dried in a vacuum oven at 55° C. to give V (0.89 g, 95% yield, HPLC purity 92.9%) as a yellow solid. $^{19}$F NMR (376 MHz, DMSO-d6): δ −83.3 (d, J=26.7 Hz), −133.7 (d, J=26.7 Hz). Also contained 2.1% of the 3,5,6-trifluoro side-product.

Example 3i. Preparation of Difluorophthalimide V (Z=CO$_2$CH$_2$Ph)

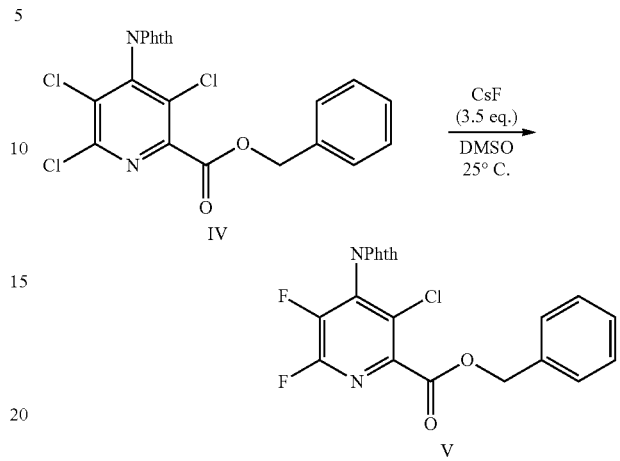

CsF (1.15 g, 7.58 mmol) was added to a 50 mL RBF equipped with stirring bar and distillation apparatus. Then 25 mL of dimethylsulfoxide (DMSO) was added. The flask was half-way merged to an oil bath. Vacuum (approximately 1 mm Hg) was connected to the distillation apparatus. Approximately 10 mL of DMSO was distilled out. Distillation apparatus was removed and the system was cooled with a nitrogen balloon. Compound IV (1.0 g, 2.17 mmol) was added in one portion. The reaction mixture was stirred at room temperature for 24 h, poured into 50 mL ice-water, stirred for 30 min and product collected. The wet cake was washed with water (2×10 mL) and hexane (10 mL) and dried in a vacuum oven at 55° C. to provide compound V (0.86 g, 93% yield, HPLC purity 88.4%) as a beige solid. $^1$H NMR (400 MHz, DMSO-d6): δ 8.10-8.18 (2H, m), 8.00-8.06 (2H, m), 7.45 (2H, m), 7.30-7.42 (3H, m), 5.42 (2H, s). $^{19}$F NMR (376 MHz, DMSO-d6): δ −83.2 (d, J=26.7 Hz), −133.0 (d, J=26.7 Hz). Also contained 0.7% % of the 6-monofluoro side-product and 7.6% of the 3,5,6-tri-fluoro side product.

Example 4a. Preparation of 4-Amino-3,6-dichloro-5-fluoropicolinic acid

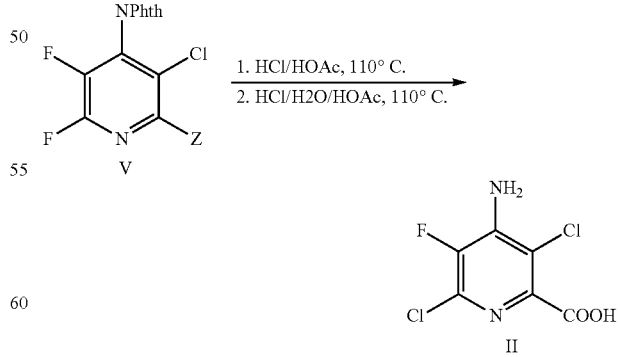

Compound V (Z=CO$_2$Me; 5.0 g, 14.2 mmol) was suspended in a solution of HCl in acetic acid (2M, 35.5 mL, 71 mmol, 5.0 eq.) in a 450 mL, sealed flask. The mixture was stirred at 110° C. (oil bath) overnight and then cooled down to 5° C. Aqueous HCl (12N, 10 mL) was added slowly to the flask, the flask was sealed again, and put into a 110° C. oil bath overnight. The resulting mixture was cooled to 5° C. and filtered. The collected solid was suspended in 100 mL of 2N aqueous HCl solution, stirred at 110° C. for 60 min, and filtered. The filtered solid was washed with hexane and dried to provide compound II (1.88 g, 51% yield) as an off-white solid. HPLC purity: 97.1%. Mp: 211.0-212.7° C.; $^1$H NMR (d$_6$-DMSO) δ 13.81 (broad s, 1H), 7.21 (broad s, 2H). $^{19}$F NMR (d$_6$-DMSO) δ −137.05.

Example 4b. Preparation of 4-Amino-6-bromo-3-chloro-5-fluoropicolinic acid

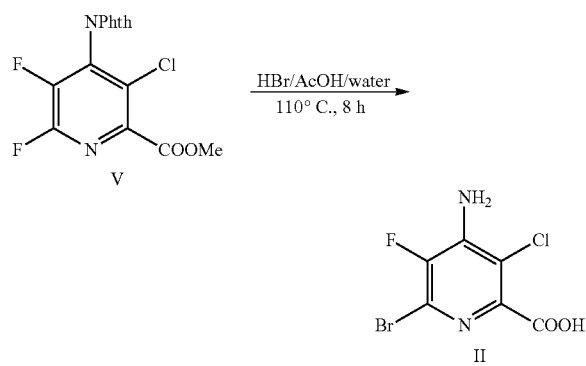

A mixture of compound V (3.92 g, 11.11 mmol), water (2 mL, 111.0 mmol, 10 eq.) and anhydrous HBr in AcOH (5.7M, 78 mL, 444.6 mmol, 40 eq.) was heated at 110° C. for 18 h in a 500 mL sealed flask. The reaction mixture was then cooled to 0° C. and quenched with water (400 mL). The resulting suspension was stirred for 30 min at 0° C., filtered and the collected solid was washed with water (2×100 mL) and hexanes (3×100 mL) to provide compound II (2.08 g, 54% yield) as a beige solid. HPLC purity: 96.5%. Mp: 211.3-212.5° C.; $^1$H NMR (d$_6$-DMSO) δ 13.72 (broad s, 1H), 7.16 (broad s, 2H). $^{19}$F NMR (d$_6$-DMSO) δ −130.28.

Example 4c. Preparation of 4-Amino-6-bromo-3-chloro-5-fluoropicolinic acid

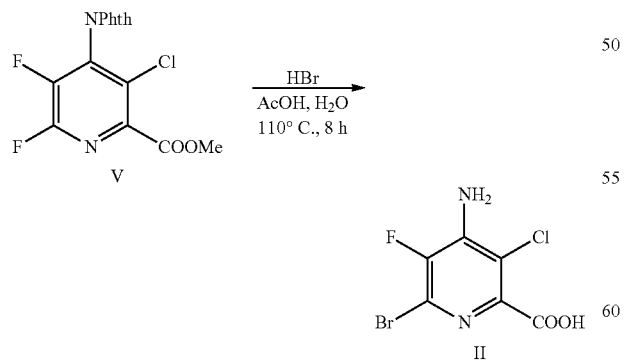

In a 1 L Hastelloy C276 reactor, compound V (50 g, 0.142 mol., 1.0 mol. eq.) was suspended in water (8.93 g, 0.496 mol., 3.5 mol. eq.) and then HBr (57.45 g, 0.71 mol., 5 mol. eq.) in acetic acid (116.6 g) was added. The reactor was heated to 110° C. with agitation and maintained at 110° C. for 8 h. The reactor was then cooled to 60° C. and filtered. The wet cake was washed with water (2×150 mL) and dried to provide compound II (42.6 g, 90% yield, 90% purity) as an off-white solid.

Example 4d. Preparation of 4-Amino-6-bromo-3-chloro-5-fluoropicolinic acid

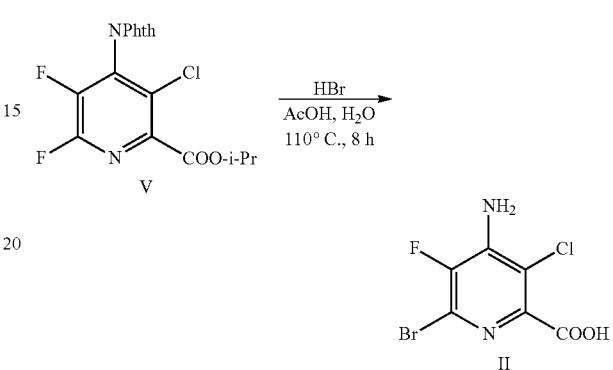

In a 1 L Hastelloy C276 reactor, compound V (Z=CO$_2$-i-Pr; 50 g, 0.13 mol., 1.0 mol. eq.) was suspended in water (8.25 g, 0.46 mol., 3.5 mol. eq.) and then HBr (53.0 g, 0.65 mol., 5 mol. eq.) in acetic acid (107.6 g) solution was added. The reactor was heated to 110° C. with agitation and maintained at 110° C. for 8 h. The reactor was then cooled to 60° C. and filtered. The wet cake was washed with water (2×150 mL) and dried to provide compound II (39.3 g, 90% yield) as an off-white solid. The HPLC purity was determined to be 90%.

Example 4e. Preparation of 4-Amino-6-bromo-3-chloro-5-fluoropicolinic acid

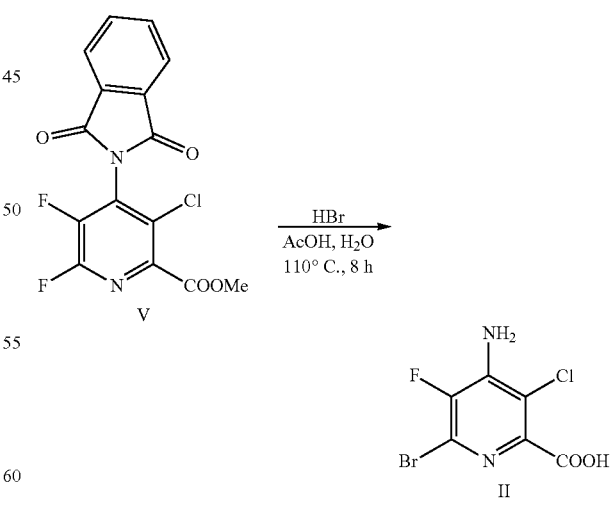

In a 1 L Hastelloy C276 reactor, compound V (Z=CO$_2$Me, Y=H; 50 g, 0.142 mol., 1.0 mol. eq.) was suspended in a mixture of water (8.93 g, 0.496 mol., 3.5 mol. eq.) and a solution of HBr (57.45 g, 0.71 mol., 5 mol. eq.) in acetic acid (116.6 g). The reactor was heated to 110° C. with agitation, maintained at temperature for 8 h., and then cooled to 60° C. and filtered. The filtered wet cake was reslurried in 50 wt % aqueous methanol (150 g) at 60° C. for 1 hr and filtered. The wet cake was dried to provide compound II (33.72 g, 87.6% yield) as an off-white solid. The HPLC purity of the isolated product was determined to be 99.1%.

Example 4f. Preparation of 4-Amino-6-bromo-3-chloro-5-fluoropicolinic acid

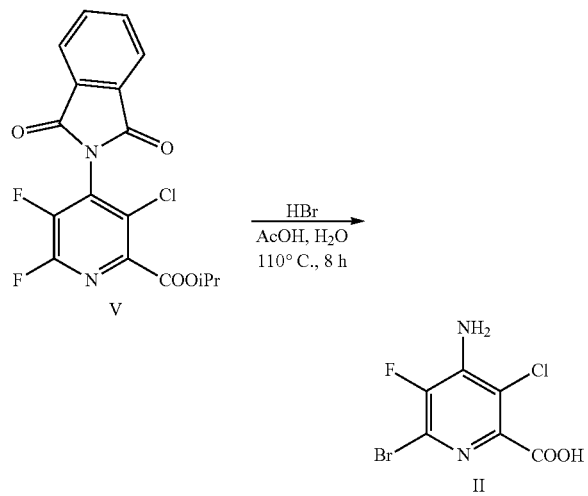

In a 1 L Hastelloy C276 reactor, compound V (Z=CO$_2$iPr, Y=H; 50 g, 0.13 mol., 1.0 mol. eq.) was suspended in a mixture of water (8.25 g, 0.46 mol., 3.5 mol. eq.) and a solution of HBr (53.0 g, 0.65 mol., 5 mol. eq.) in acetic acid (107.6 g). The reactor was heated to 110° C. with agitation, maintained at temperature for 8 h., and then cooled to 60° C. and filtered. The filtered wet cake was reslurried in 50 wt % aqueous methanol (150 g) at 60° C. for 1 hour and filtered. The wet cake was dried to provide compound II (31.42 g, 88.2% yield) as an off-white solid. The HPLC purity of the isolated product was determined to be 99.0%.

Example 4g. Preparation of 4-Amino-6-bromo-3-chloro-5-fluoropicolinic acid

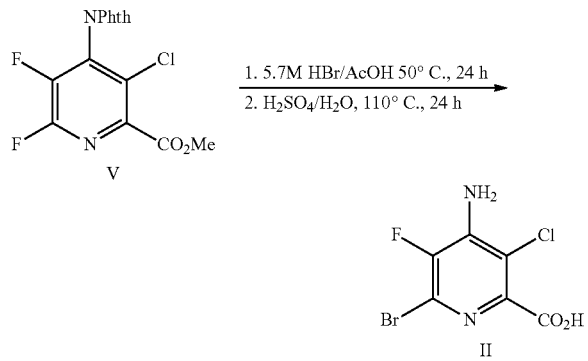

Step 1:
Chemglass high pressure vessel (75 mL) equipped with magnetic stirrer was charged with compound V (5.0 g, 14.18 mmol, 1 equiv) and HBr in AcOH (5.7M, 25 mL, 141.8 mmol, 10 equiv). The flask was sealed with PTFE cap and heated at 50° C. for 24 h. The reaction mixture was cooled down to 0° C. and quenched with water (50 mL). The suspension was stirred for 30 min at rt, filtered, the solid was washed with water (2×30 mL) and dried.

Step 2:
To the crude mixture was added 40 mL of H$_2$SO$_4$/H$_2$O (2:1 v/v). The mixture was stirred at 110° C. for 24 h, cooled to 0° C. and quenched with water (200 mL). The suspension was stirred for 30 min at room temperature, filtered. The solid was suspended in 200 mL of water, heated at 110° C. for 1 h, filtered hot suspension and dried to obtain compound II (2.67 g, 70% yield, 2 steps). HPLC purity: 90.3%.

Example 4h. Preparation of 4-Amino-3,6-dichloro-5-fluoropicolinic acid

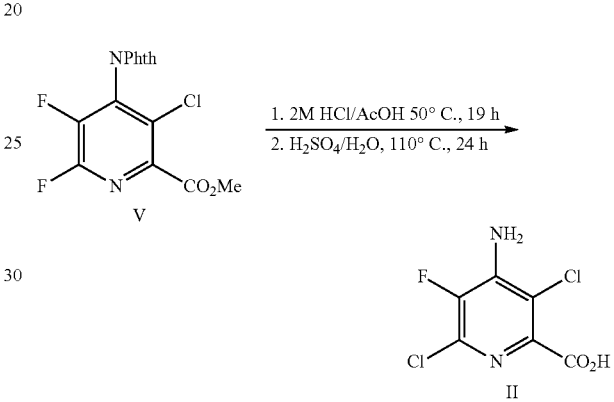

Step 1:
Compound V (2.5 g, 7.1 mmol, 1.0 eq.) was suspended in HCl in HAc (2M, fresh made in house and dry HCl bubbled through, 17.5 mL, 35 mmol, 5.0 eq.) in a 75 mL glass sealed flask. The mixture was stirred at 90° C. oil bath for 19 h. The reaction mixture was cooled down to 5° C., opened the flask carefully, poured into 60 mL of ice water, stirred for 30 min, filtered. The white solid was 4.5 g (wet) and used in the next reaction without further purification.

Step 2:
To the crude mixture was added 20 mL of H$_2$SO$_4$/H$_2$O (2:1 v/v). The mixture was stirred at 110° C. for 24 h, cooled to 0° C. and quenched with water (100 mL). The suspension was stirred for 30 min at room temperature, filtered. The solid was suspended in 100 mL of water, heated at 110° C. for 1 h, filtered hot suspension and dried to obtain compound II (1.10 g, 60% yield, 2 steps). HPLC purity: 91.4%.

Example 5a. Preparation of benzyl 4-amino-6-bromo-3-chloro-5-fluoropicolinate

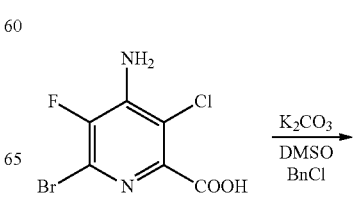

-continued

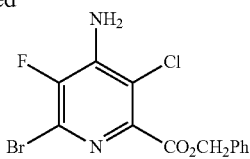

A 125 mL three-neck flask equipped with a magnetic stirrer, a cold water condenser, a thermocouple and a nitrogen pad, was charged with 4-amino-6-bromo-3-chloro-5-fluoropicolinic acid (5.0 g, 18.56 mmol) and dimethyl sulfoxide (20 mL). The mixture was stirred and powdered $K_2CO_3$ (2.82 g, 20.41 mmol, 1.1 eq) was added in portions over 10 min (a mild exotherm was observed with the temperature rising from 20 to 22.5° C.). After the mixture was stirred at ambient temperature for 30 min, benzyl chloride (2.59 g, 20.41 mmol, 1.1 eq) was added in one portion. The resulting mixture was stirred at ambient temperature for 15 min, 40° C. for 5 h, and 50° C. for 2 h. Then, the reaction mixture was cooled to ambient temperature, water (75 mL) was added and the resulting mixture was stirred for 30 min. The solid present was filtered, rinsed with water (20 mL), suction-dried and dried in vacuum oven at 50° C. overnight to give the benzyl ester, 6.5 g (97% yield). $^1$H-NMR (500 HMz/CDCl$_3$) δ 7.44 (m, 2H), 7.35 (m, 3H), 5.40 (s, 2H), 4.98 (s, br, 2H). $^{19}$F-NMR δ −129.16.

Example 5b. Preparation of benzyl 4-amino-6-bromo-3-chloro-5-fluoropicolinate

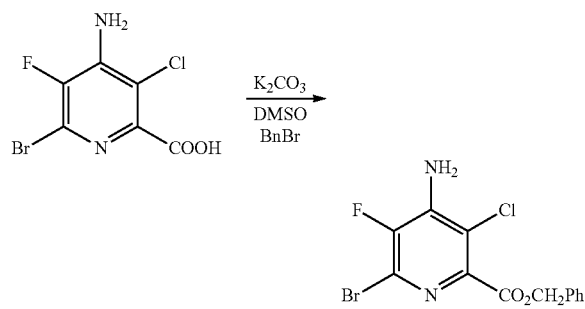

A sample of 4-amino-6-bromo-3-chloro-5-fluoropicolinic acid (12.87 g, 82 wt % purity as estimated by $^1$H NMR, 39.17 mmol, containing 18 wt % (13.94 mmol) of phthalic acid) was dissolved in DMSO (100 mL) in a 250-mL three-neck flask equipped with a magnetic stirrer, a cold water condenser, a thermocouple and a nitrogen pad. Powdered $K_2CO_3$ (9.95 g, 72 mmol) was added in portions over 10 min, resulting in a mild exothermic reaction with the temperature rising from 20 to 25° C. The mixture was stirred at ambient temperature for 30 min, then benzyl bromide (8.00 g, 46.8 mmol) was slowly added over 10 min while the temperature was maintained below 25° C. with a cold water bath. The resulting mixture was stirred at ambient temperature for 4 h, then was poured into 300 mL of cold water. The resulting slurry was stirred for 15 min, filtered and rinsed with 100 mL of water. After suction drying, the crude product was washed with hexane (100 mL), and dried at 45° C. in a vacuum overnight to provide the benzyl ester 13.40 g (95% yield).

Example 5c. Preparation of benzyl 4-amino-6-bromo-3-chloro-5-fluoropicolinate

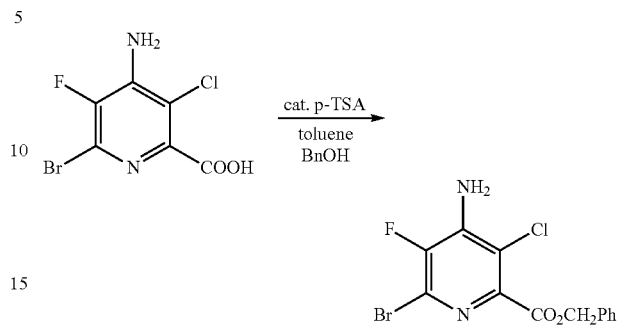

To a three-neck flask equipped with a stir bar, a heating mantle, and a Dean-Stark trap with condenser, was added 4-amino-6-bromo-3-chloro-5-fluoropicolinic acid (3.00 g, 11.13 mmol), benzyl alcohol (11.48 g, 10 eq), toluene, and p-toluenesulfonic acid monohydrate (p-TSA, 212 mg, 0.1 eq). The mixture was heated at 80° C., and slowly placed under a vacuum of 30 mm Hg in order to remove water that was generated in situ. After heating at 80° C. for 10 h, the reaction mixture was cooled to ambient temperature. Cyclohexane (50 mL) was added dropwise and the resulting slurry was stirred for 2 h, cooled to 10° C., filtered and the wet cake was rinsed with cyclohexane (10 mL). The wet cake was then washed with water (20 mL), suction dried, rinsed with cyclohexane (5 mL), and dried at 45° C. under reduced pressure in a vacuum oven to provide 3.29 g (82.3% yield) of the benzyl ester.

Example 5d. Preparation of cyanomethyl 4-amino-6-bromo-3-chloro-5-fluoropicolinate

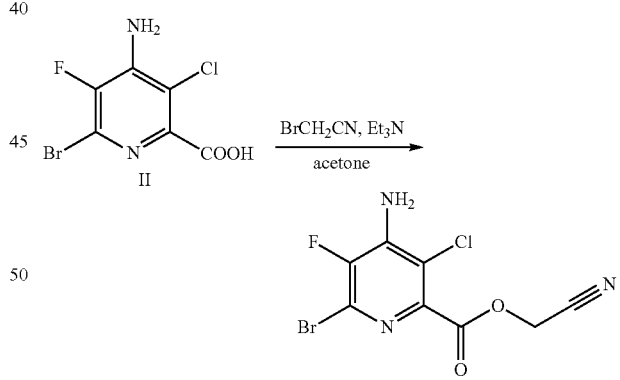

A 125 mL round bottom flask equipped with a magnetic stir bar was charged with 4-amino-6-bromo-3-bromo-5-fluoropicolinic acid (2.0 g, 7.42 mmol) and acetone (30 mL). Bromoacetonitrile (1.034 mL, 14.84 mmol) was added followed by dropwise addition of triethylamine (4.14 mL, 29.7 mmol). A white precipitate formed, and additional acetone (10 mL) was added. After 25.5 h, additional triethylamine (1.035 mL, 7.42 mmol), bromoacetonitrile (0.517 mL, 7.42 mmol) and acetone (10 mL) were added. The reaction mixture was stirred for an additional 22.5 h and then the volatiles were removed under reduced pressure. The crude material was re-suspended in EtOAc and washed with water.

The layers were separated and the organic layer was dried (Na$_2$SO$_4$), filtered, and concentrated under reduced pressure to provide cyanomethyl 4-amino-6-bromo-3-chloro-5-fluoropicolinate (1.365 g, 4.42 mmol) in 60% yield as an off-white solid. $^1$H NMR (600 MHz, DMSO-d$_6$) δ 7.34 (s, 2H), 5.27 (s, 2H). $^{19}$F NMR (564 MHz, DMSO-d$_6$): δ −127.73.

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. The compound of the formula:

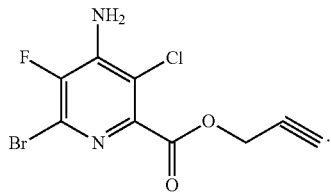 [SMILES: C#CCOC(=O)c1nc(Br)c(F)c(N)c1Cl]

2. The compound of the formula:

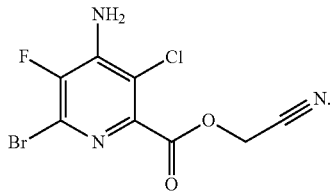 [SMILES: N#CCOC(=O)c1nc(Br)c(F)c(N)c1Cl]

3. The compound of the formula:

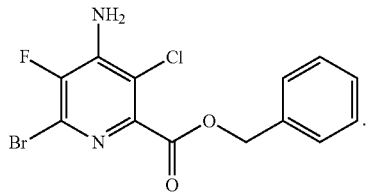 [SMILES: Nc1c(F)c(Br)nc(C(=O)OCc2ccccc2)c1Cl]

* * * * *